US012797575B2

(12) United States Patent
Signore et al.

(10) Patent No.: US 12,797,575 B2
(45) Date of Patent: Nov. 17, 2026

(54) DEVICE AND METHOD FOR SEALING A CATHETER PART INTO A FILM SLEEVE

(71) Applicant: Harro Hoefliger Verpackungsmaschinen GmbH, Allmersbach im Tal (DE)

(72) Inventors: Andreas Signore, Allmersbach im Tal (DE); Kevin Schwarz, Allmersbach im Tal (DE); Maik Müller, Allmersbach im Tal (DE)

(73) Assignee: Harro Hoefliger Verpackungsmaschinen GmbH, Allmersbach im Tal (DE)

( * ) Notice: Subject to any disclaimer, the term of this patent is extended or adjusted under 35 U.S.C. 154(b) by 37 days.

(21) Appl. No.: 19/059,017

(22) Filed: Feb. 20, 2025

(65) Prior Publication Data

US 2025/0269141 A1 Aug. 28, 2025

(30) Foreign Application Priority Data

Feb. 23, 2024 (EP) .................................... 24159466

(51) Int. Cl.

| | |
|---|---|
| ***B29C 65/02*** | (2006.01) |
| ***A61M 25/00*** | (2006.01) |
| ***B29C 65/00*** | (2006.01) |
| ***B29C 65/18*** | (2006.01) |
| ***B29C 65/78*** | (2006.01) |

(Continued)

(52) U.S. Cl.

CPC ..... *A61M 25/0012* (2013.01); *B29C 65/7802* (2013.01); *B29C 65/7832* (2013.01); *B29C 65/7861* (2013.01); *B29C 65/7888* (2013.01); *B29C 65/7891* (2013.01);

(Continued)

(58) Field of Classification Search

CPC ......... B29C 65/02; B29C 65/18; B29C 65/78; B29C 65/7802; B29C 65/7832; B29C 65/7861; B29C 65/7888; B29C 65/7891; B29C 65/7894; B29C 66/433; B65B 11/50; B65B 47/04; B65B 47/06; B65B 51/26; B65B 51/303; B65B 61/06

USPC ......... 264/248; 425/289, 408, 514; 156/292, 156/510; 53/450, 545

See application file for complete search history.

(56) References Cited

U.S. PATENT DOCUMENTS 3,323,274 A * 6/1967 Justus ..................... B29C 65/02 156/292 X
5,048,684 A * 9/1991 Scott .................... B65D 75/323 206/364 X (Continued)

FOREIGN PATENT DOCUMENTS

GB 607796 A 9/1948
GB 2466523 A 6/2010

*Primary Examiner* — Leo B Tentoni
(74) *Attorney, Agent, or Firm* — Walter Ottesen, P.A.

(57) ABSTRACT

A device and a method are for sealing a catheter part into a film sleeve. Molding plates are provided with molding indentations which have a one-dimensionally curved cross-sectional shape. In molding stations, base and cover film sections are placed without strain into the molding indentations. In an introduction station, at least one catheter part is introduced into a corresponding molding indentation. In a sealing station, the catheter part is sealed into a film sleeve by the base film section and the cover film section being sealed onto one another at common sealing sections and being sealed onto sealing faces of the catheter part while forming the film sleeve.

11 Claims, 4 Drawing Sheets

(51) Int. Cl.

| | |
|---|---|
| ***B65B 11/50*** | (2006.01) |
| ***B65B 47/04*** | (2006.01) |
| ***B65B 47/06*** | (2006.01) |
| ***B65B 51/26*** | (2006.01) |
| ***B65B 51/30*** | (2006.01) |
| ***B65B 61/06*** | (2006.01) |

(52) U.S. Cl.
CPC ........ *B29C 65/7894* (2013.01); *B29C 66/433* (2013.01); *B65B 51/303* (2013.01)

(56) References Cited

U.S. PATENT DOCUMENTS

| | | | |
|---|---|---|---|
| 5,497,601 | A | 3/1996 | Gonzalez |
| 2011/0078981 | A1 | 4/2011 | Bongers-Ambrosius et al. |

* cited by examiner

*Fig. 6*
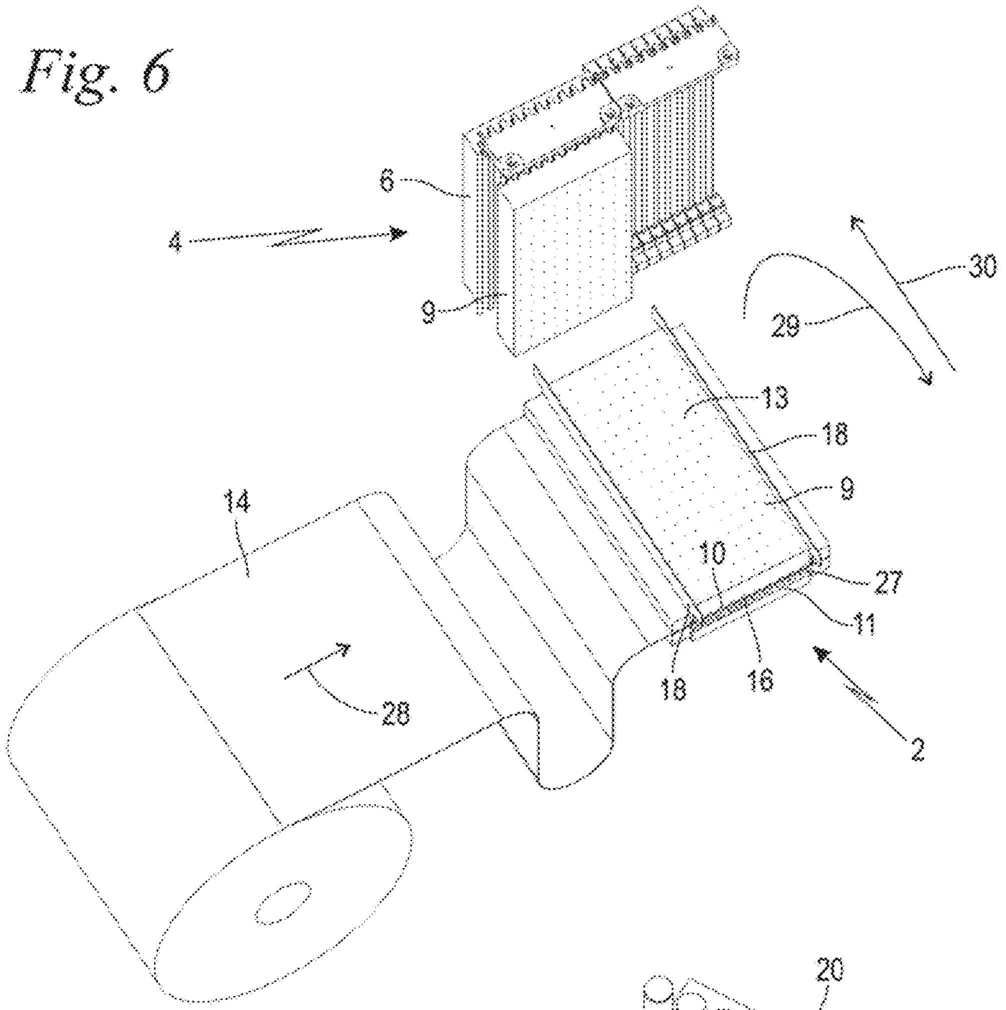
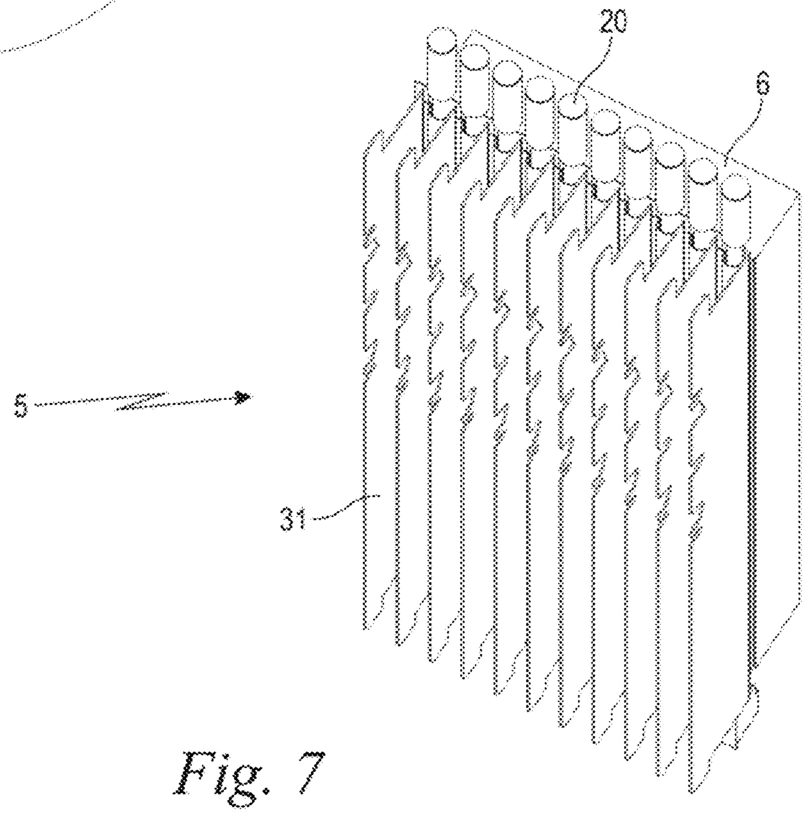
*Fig. 7*

DEVICE AND METHOD FOR SEALING A CATHETER PART INTO A FILM SLEEVE

CROSS-REFERENCE TO RELATED APPLICATIONS

This application claims priority of European patent application no. 24159466.2, filed Feb. 23, 2024, the entire content of which is incorporated herein by reference.

TECHNICAL FIELD

The disclosure relates to a device and a method for sealing at least one catheter part into a film sleeve.

BACKGROUND

Catheters, in particular for medical applications, need to be stored sterilely before use. In particular, film tubes or film sleeves into which such a catheter can be fully or partly sealed are suitable for this. A problem in this case is to form a film sleeve with a specific dimensional accuracy, stringent leak-tightness requirements having to be satisfied particularly at the sealing points.

SUMMARY

It is an object of the disclosure to provide a device which enables reliable and accurately reproducible formation of film sleeves with high quality, particularly in respect of the sleeve volume and leak-tightness, and sealing of the catheter part with corresponding quality.

This object is achieved by various embodiments of devices according to the disclosure.

It is a further object of the disclosure to provide a corresponding method with which high-quality sealing is possible.

This object is achieved by a various embodiments of methods according to the disclosure.

The term "catheter part" selected and used here in connection with the disclosure refers to a catheter in its entirety as well as parts or components thereof, such as connecting parts or the like.

The disclosure provides a device for sealing at least one catheter part into a film sleeve, which includes a first molding station, a second molding station, an introduction station for introducing the catheter part, and a sealing station for sealing a base film section and a cover film section onto one another and onto sealing faces of the catheter part while forming the film sleeve. The device furthermore includes a first molding plate having at least one first molding indentation for the base film section and a second molding plate having at least one second molding indentation for the cover film section, the first molding indentation and the second molding indentation having a one-dimensionally curved cross-sectional shape in the region of the base film section and of the cover film section, respectively. In addition, the device includes first placement arrangement for strain-free placement of the base film section into the at least one first molding indentation, as well as second placement arrangement for strain-free placement of the cover film section into the at least one second molding indentation.

In a corresponding method according to the disclosure, the following method steps are carried out:

in the first molding station, a base film section is placed without strain into at least one first molding indentation of a first molding plate, in an introduction station, at least one catheter part is introduced with the base film section put in place into a corresponding first molding indentation, in the second molding station, a cover film section is placed without strain into at least one second molding indentation of a second molding plate, in the sealing station, the catheter part is sealed into a film sleeve by the first molding plate and the second molding plate being brought together with the base film section put in place, with the cover film section put in place and with the catheter part introduced, the base film section and the cover film section being sealed onto one another at common sealing sections and being sealed onto sealing faces of the catheter part while forming the film sleeve.

The disclosure is based on the principle of molding film sections to form a film sleeve without—in contrast to the deep-drawing method—subjecting the flat film material to a tensile and/or shear deformation in the material plane. In particular, no plastic deformation of the film material takes place during the molding in the molding indentations. Rather, the one-dimensionally curved cross-sectional shape of the molding indentations leads to the same curvature of the respective base film section, or of the cover film section. A one-dimensional curvature is a curvature without spherical curvature components, that is, a curvature such as that which for example a sheet of paper may assume without creasing. The deformation of the film material is reduced to a pure bending deformation. Since the thickness of the films employed is small in comparison with their other dimensions, the corresponding bending deformations and the resulting strain components in the technical sense are at most small and substantially negligible. Overall, in the technical sense strain-free placement into the mold and strain-free shaping of the film sections therefore take place. This leads to high dimensional accuracy and accurate reproducibility. The film sections brought into shape fold-free and essentially stress-free may be sealed exactly onto one another and onto corresponding sealing regions of the catheter part, so that the required leak-tightness can be achieved with high reliability.

It may be expedient to form only a single molding indentation in each of the individual molding plates. In an embodiment, a plurality of first molding indentations are formed in the first molding plate and a corresponding number of second molding indentations are formed in the second molding plate. This enables the shaping, the insertion of parts, the sealing and optionally also the separation of a plurality of units respectively in only one assigned station.

The placement of the film sections into the molding indentations may, for example, take place by suitable vacuum guiding. Advantageously, the first placement arrangement and/or the second placement arrangement are configured as pressing dies corresponding with the first and second molding indentations, respectively. In this way, exact placement of the film sections into the molding indentations may be achieved with simple means. By corresponding resilient mounting and/or movement control, sequential placement into a plurality of molding indentations of a molding plate may be performed, which enables strain-free feeding of a sufficient amount of film.

In an expedient development, the first and/or second molding plates are provided with holding arrangements for holding the base film section put in place in the first molding indentation and the cover film section put in place in the second molding indentation, respectively. At least for a part of the process, these may be the aforementioned placement arrangements, or pressing dies. Preferably, the holding arrangements are configured in the form of a reduced-pressure supply. When a reduced pressure is applied, the reduced-pressure supply ensures that the film sections bear cleanly on the surface of the molding indentations. At the same time, there is no space requirement for this inside the molding indentations, so that the corresponding catheter part can be put in place and sealed unimpeded.

In the scope of the invention, various cross-sectional shapes of the molding indentations may be envisioned. Preferably, the first and/or second molding indentations are configured in the form of a half-cylinder. With a correspondingly cylindrical shape of the catheter part, its rotational angle setting is unimportant during the introduction and the sealing, so that the process is simplified.

For the continuous or cyclic processing of the films, continuous film webs, separated film sheets or combinations thereof may be envisioned. In an embodiment, a cutting arrangement is provided for separating the base film section and the cover film section, respectively, from a continuous film web, and in particular is arranged in at least one of the two molding stations. The production and use of separated film sheets produces additional possibilities for movement of the components of the individual handling stations. In particular, a correspondingly equipped molding plate may be guided easily relative to the respective other molding plate so that the two can be pressed together in the sealing station in order to carry out the sealing procedure.

Expediently, a sealing heater is integrated in at least one of the two molding plates. The corresponding molding plate therefore fulfills in a twofold function not only the function of shaping but also the function of sealing. The expense of, for example, separate sealing jaws is thereby obviated.

In the scope of the disclosure, it may be advantageous to manufacture an uninterrupted, contiguous web of sealed catheter parts. In an embodiment, the device includes a separating station for separating a plurality of sealed catheter parts. In this way, on the one hand the process reliability during the processing of an uninterrupted product strip may be used during the shaping, placement and sealing, while on the other hand individual products ready for use are available after the separating station.

BRIEF DESCRIPTION OF DRAWINGS

The invention will now be described with reference to the drawings wherein:

FIG. 6 shows a detail representation of the second molding station and the sealing station according to FIG. 1 during the molding and sealing of the cover film section; and, FIG. 7 shows a perspective view of a part of the separating station according to FIG. 1 with a row of film blades during the separation of the sealed catheter parts.

DETAILED DESCRIPTION

Figure 1:
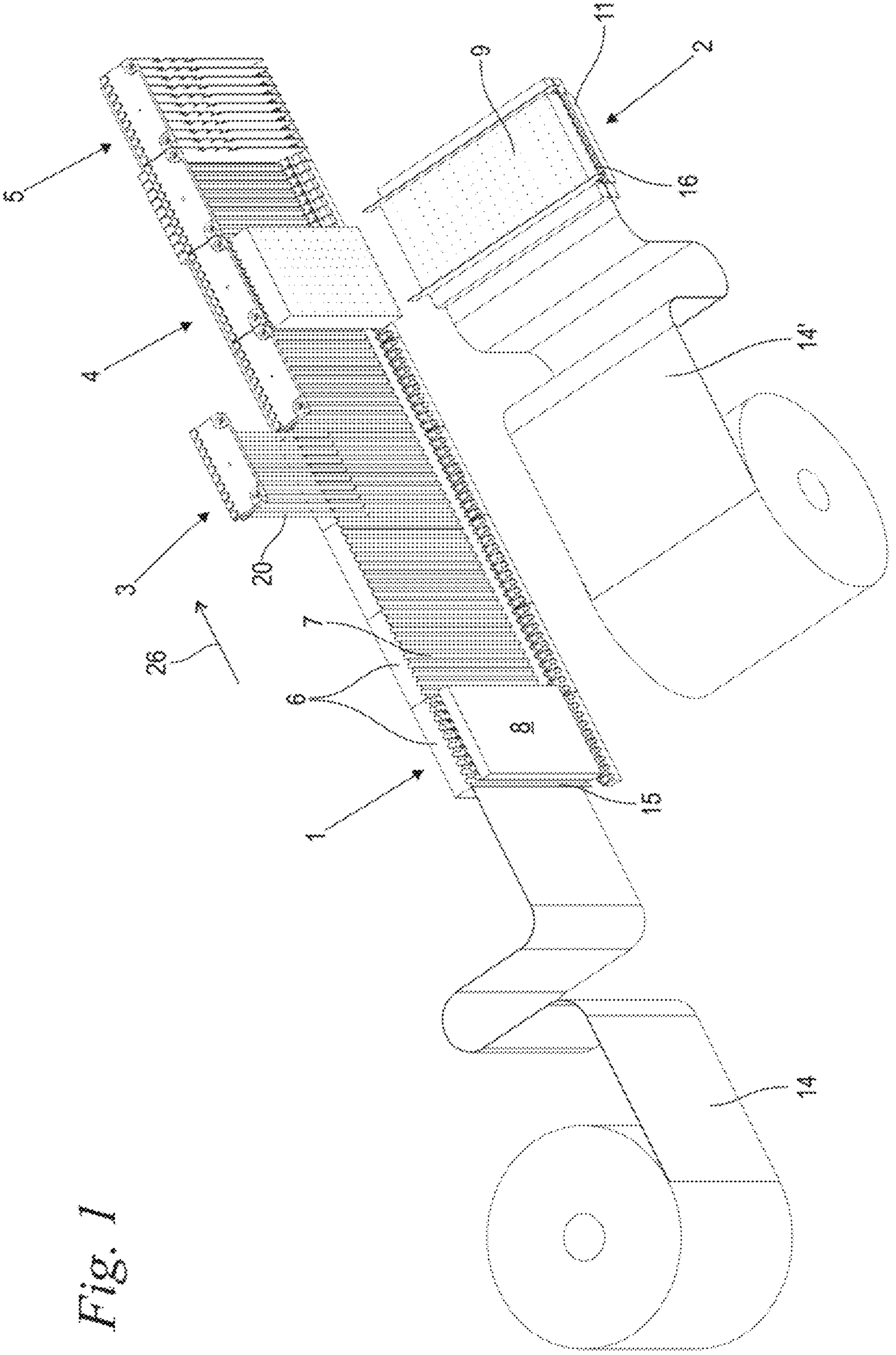
FIG. 1 shows a perspective partial view of a device configured according to the disclosure with two molding stations, with an introduction station, with a sealing station and with a separating station.
Figure 2:
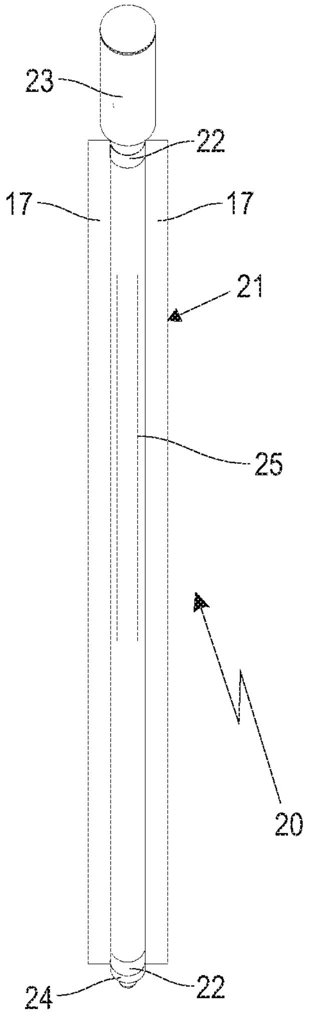
FIG. 2 shows a schematic representation of a catheter part sealed into a film sleeve with the device according to FIG. 1.
Figure 2:
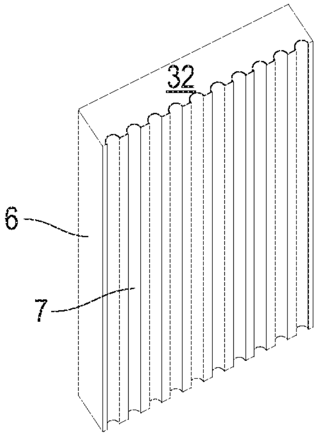

FIG. 1 shows a perspective partial view of a device configured according to the disclosure for sealing a catheter part 20, which is represented in FIG. 2, into a film sleeve 21. With reference to FIG. 2, the term “catheter part” 20 selected here refers in the embodiment shown to a complete catheter unit having a catheter tube 25 (only indicated), having a connecting piece 23 and having a head piece 24. In the scope of the disclosure, the catheter part 20 may however also be formed only by one or more parts of the aforementioned complete catheter unit.

The catheter part 20 is partially sealed in the manner according to the disclosure into a film sleeve 21. For this purpose, the film sleeve 21 is formed from a base film section 15 and from a cover film section 16 (FIG. 1). The cover film section 16 is sealed onto the base film section 15 along two sealing sections 17 running parallel to one another on either side of the catheter tube 25, so that the vasiform film sleeve 21 is formed. The latter is in turn sealed at its two ends onto closed circumferential sealing faces 22 of the catheter part 20, so that the region of the catheter part 20 enclosed by the film sleeve 21 is shielded tightly from the environment and can be kept sterile. The disclosure likewise includes the sealing of individual parts or modules of the catheter unit, that is, for example, sealing of the connecting piece 23, of the head piece 24 and/or of further parts, which are then to be understood as a catheter part 20 in the context here.

Again with reference to FIG. 1, it may be seen that the device according to the disclosure is configured as a so-called oval runner. Here, a row of first molding plates 6 is moved linearly on a closed circumferential path past various stations and is subsequently moved back parallel thereto. The movement may be intermittent with stops at the individual stations, or otherwise it may be continuous. For the sake of simplicity, the only section of the device shown is the one in which the first molding plates 6 receive base film sections 15 from a continuous film web 14 and are displaced together therewith in the direction of an arrow 26 along various stations, here in order along a first molding station 1, an introduction station 3, a sealing station 4 and a separating station 5.

In the first molding station 1, shaping of the base film sections 15 takes place. In the subsequent introduction station 3, catheter parts 20 are introduced into the prepared first molding plates 6. In parallel therewith, cover film sections 16 are formed from a further continuous film web 14', supplied to a second molding station 2 and molded there in a second molding plate 9. The second molding plate 9 does not participate in the above-described oval runner movement of the first molding plates 6, but instead is moved to and fro cyclically between the second molding station 2 and the sealing station: after the molding of a cover film section 16, the second molding plate 9 with the cover film section 16 held therein is moved to the sealing station 4 and brought together there with a corresponding first molding plate 6. Here, the respective base film section 15 and the cover film section 16 are sealed onto one another and sealed with the catheter part 20, so that an initially contiguous web of sealed catheter parts 20 is created. While the second molding plate 9, now empty, is being moved back to the second molding station 2, the first molding plate with a contiguous row of sealed catheter parts 20 held therein is moved further to the separating station 5, where the catheter parts 20 are finally separated into the form shown in FIG. 2.

Figure 3:
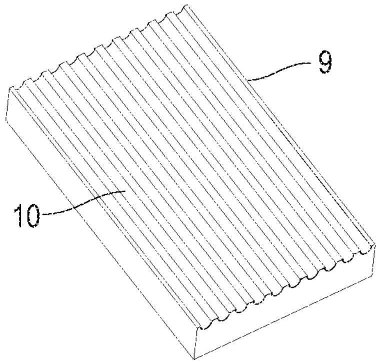
FIG. 3 shows a perspective diagrammatic representation of a molding plate for the base film section and a molding plate for the cover film section.

FIG. 3 shows a perspective diagrammatic representation of details of a first molding plate 6 for the base film section 15 and of a second molding plate 9 for the cover film section 16. At least one first molding indentation 7 is formed in the first molding plate 6. In the present case there are a plurality, here ten, of first molding indentations 7 lying parallel to one another in the first molding plate. The characteristic feature of these first molding indentations 7 is that they have a one-dimensionally curved cross-sectional shape. This may be elliptical, oval, frustoconical or even angular. In the embodiment shown, the cross section is semicircular. In other words, the first molding indentation 7 is configured in the form of a half-cylinder. Corresponding shaping of the base film section 15 placed therein therefore takes place strain-free without elastic or even plastic deformation of the film material in the plane of the film, that is, without strain and/or shear deformation in the plane of the film. The same applies similarly for a corresponding number of second molding indentations 10 in the second molding plate 9 and the cover film section 16 molded therein.

FIG. 3 also indicates that a sealing heater 32, which is employed in the sealing station 4 described in more detail below, is arranged in the first molding plate 6. The second molding plate 9 may also be equipped with such a sealing heater. Naturally, other forms of the sealing are also conceivable in the scope of the disclosure.

Figure 4:
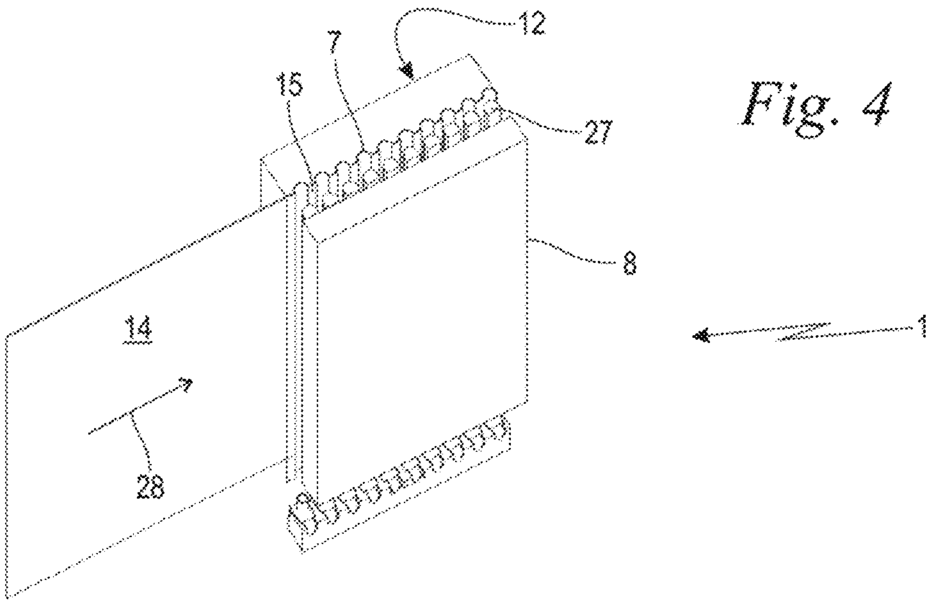
FIG. 4 shows an individual representation of the first molding station according to FIG. 1 with a molding plate according to FIG. 3 and with pressing dies applied during the placement of the base film section.

FIG. 4 shows a schematic individual representation of the first molding station 1 according to FIG. 1 with a first molding plate 6 according to FIG. 3. There, a part of the continuous film web 14 is initially placed as a base film section 15 onto the first molding plate 6 with its first molding indentations 7. The individual base film sections 15 of the individual molding plates 6 maintain their property as a contiguous film web 14 during this until the separating station 5. After the base film section 15 has been placed on, it is shaped by strain-free placement into the first molding indentations 7 via first placement arrangement 8.

The first placement arrangement 8 may be a controlled reduced-pressure supply or the like, and in the embodiment shown they are configured as a row of pressing dies 27 which correspond in shape, position and number with the first molding indentations 7. It is conceivable to press the base film section 15 simultaneously into all the molding indentations 7 of the molding plate 6. In the present case this is done sequentially. Specifically, it may be seen in FIG. 4 that the pressing die 27 on the right in the image, that is, furthest away from the stock roll of the film web 14, is projecting furthest from an associated base plate and is protruding into the corresponding molding indentation. Starting from this, the further pressing dies 27 spring back in the manner of a staircase. All the pressing dies 27 are moreover mounted resiliently flexibly. The aforementioned base plate is thus then moved toward the molding plate 6. The pressing dies then sequentially enter the corresponding molding indentations 7 in succession. When it enters, the respective pressing die 27 presses the corresponding part of the base film section 15 into the associated molding indentation 7.

So that the base film section can follow the curved cross-sectional contour of the molding indentations 7 without strain, a larger film length is required than the length of the base film section 15 bearing flatly and undeformed on the first molding plate 6. The additional amount of film necessary for this is fed, or automatically drawn, without strain from the film web 14 according to the arrow 28, since the neighboring pressing dies 27 in the direction of the supplied film web 14 are introduced less deeply and therefore do not hinder a film feed. Starting from the pressing die which is projecting furthest and therefore enters first, the base film section 15 can in this way be pressed sequentially into all the molding indentations 7 of the first molding plate without a technically relevant strain of the film material occurring.

Furthermore, the first molding plate 6 also has a holding arrangement for holding the base film section 15 put in place in the first molding indentation 7, these not being represented in more detail here but being configured in a similar way to the holding arrangement for the cover film section 16 put in place in the second molding indentation 10 according to FIG. 6, in the form of a reduced-pressure supply 12, 13. The base film section 15 molded in the manner described above is thereby suctioned into the molding indentations 7 and remains held in position there during the subsequent process steps.

Figure 5:
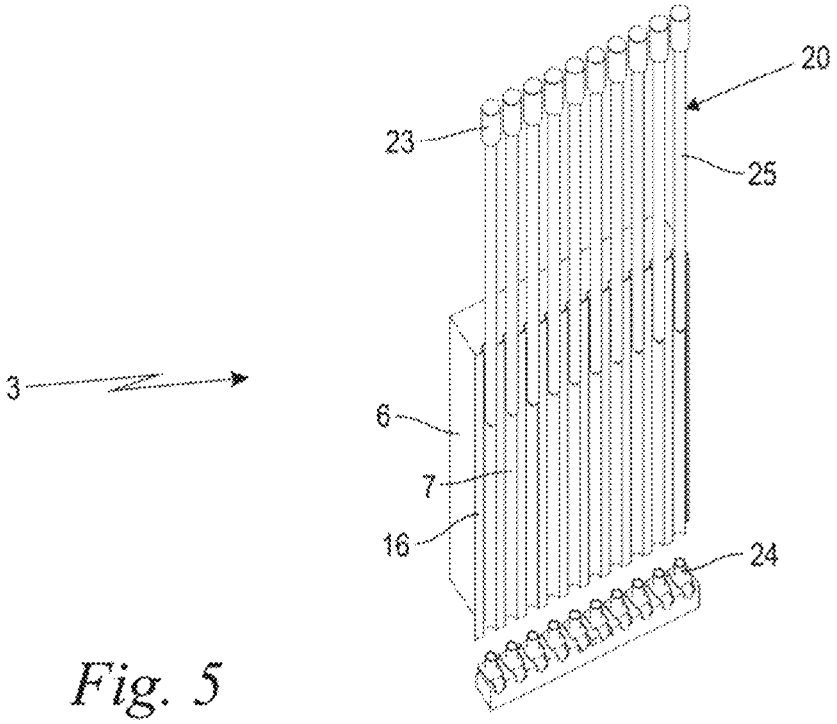
FIG. 5 shows an individual representation of the introduction station according to FIG. 1 during the introduction of a plurality of catheter parts.

FIG. 5 shows an individual representation of the introduction station 3 according to FIG. 1 during the introduction of a number of catheter parts 20 corresponding to the number of molding indentations 7. In addition to the base film section 15 put in place, the catheter parts 20 are now introduced into the molding indentations 7. Various possibilities may be envisioned for this. In the present case, a catheter tube 25 is in each case connected to a connecting piece 23 and they are introduced together from above into the respective molding indentation 7. According to FIG. 5, this is done simultaneously. Nevertheless, sequential or time-offset introduction may also be provided. The associated head pieces 24 are introduced from below into the respective molding indentation 7. Furthermore, further parts to be put in place may also be placed into the molding indentations at this introduction station or at one or more further introduction stations. It is also conceivable that, for example, only a pair of parts formed by the connecting piece 23 and the head piece 24 or a group of parts, respectively, forms the relevant catheter part 20 to be put in place in the sense of the definition according to the disclosure, and that further parts such as the catheter tube 20 are only introduced later after the sealing process described below.

FIG. 6 shows a detail representation of the second molding station 2 and the sealing station 4 according to FIG. 1 during the molding and sealing of the cover film section 16. In the second molding station 2, the second molding plate 9 already shown in FIG. 3 has its second molding indentations 10 turned downward, second placement arrangement 11 for strain-free placement of the cover film section 16 into the second molding indentation 10 being located underneath. The second placement arrangement 11 is configured in a similar way to the first placement arrangement 8 (FIG. 4) as pressing dies 27 corresponding with the second molding indentations 10. The strain-free placement of the cover film section 16 into the second molding indentations 10 with strain-free feeding of film material from the film web 14 takes place in the same way as described above in connection with the base film section 15 (FIG. 4).

A difference, however, is that the cover film sections 16 do not remain contiguous according to the embodiment, but instead cutting arrangements 18 are respectively arranged in the second molding station on either side of second molding plate 9, and these cut and therefore separate the cover film section 16 assigned to the molding plate 9 from the continuous film web 14. The separation may be performed after the molding. Alternatively, it may also be expedient initially to carry out the separation of the cover film section 16 via the cutting arrangement 18, the shaping only taking place after this. A sufficient oversize is then to be provided, from which the film material additionally required during the shaping can be drawn without strain into the second molding indentations 10.

In the scope of the disclosure, it may be expedient to separate the base film sections 15 as well. Likewise, it is conceivable to leave the cover film sections 16 as well as the base film sections 15 as a contiguous, uninterrupted film web 14' at least until the separating station.

It may also be seen in FIG. 6 that the second molding plate 9 is provided with numerous bores. In this way, a reduced pressure can be delivered into the second molding indentations 10 in order to hold the molded cover film section 16 in the molding indentations 10 after the molding procedure. The holding arrangement is thereby formed as a reduced-pressure supply 13. Similar considerations apply for the holding arrangement on the first molding plates 6 in the form of the reduced-pressure supply 12 already mentioned above.

Starting from the state described above, the second molding plate 9 with the molded cover film section 16 held therein is then set upright according to an arrow 29 in a position parallel to the first molding plates 6 and then displaced toward the sealing station 4 according to an arrow 30. There, it encounters a corresponding first molding plate 6, which in the manner described above has received a base film section 15 as well as the aforementioned catheter parts 20 in its first molding indentations 7 and holds them ready there. The second molding plate 9 is placed onto the first molding plate 6 so that the cover film section 16 and the base film section 15 bear on one another in the region of the sealing sections 17 (FIG. 2) while enclosing the catheter parts 20 put in place. In this state, the sealing procedure then takes place in particular under the action of the sealing heater 32 (FIG. 3), the sealing, or more precisely the hot sealing, then being carried out by using a hot melt adhesive at the sealing sections 17 and on the sealing faces 22 (FIG. 2).

After the sealing procedure, the second molding plate 9 is displaced back into its initial position of the second molding station 2.

The now sealed unit consisting of a base film section 15, cover film section 16 and catheter parts 20 remains in the first molding plate 6 and is displaced further together therewith after the sealing procedure to the subsequent separating station 5. FIG. 7 also shows a perspective view of a part of this separating station 5. Here, a row of film blades 31 is provided, which cut through the double film layer consisting of the base film section 15 and the cover film section 16 between the catheter parts and also outside the latter, and therefore separate the sealed catheter parts into the form shown in FIG. 2.

It is understood that the foregoing description is that of the preferred embodiments of the invention and that various changes and modifications may be made thereto without departing from the spirit and scope of the invention as defined in the appended claims.

The invention claimed is:

1. A device for sealing a catheter part into a film sleeve, the device comprising:

a first molding station;

a second molding station;

a sealing station for sealing a base film section and a cover film section onto one another and onto sealing faces of the catheter part while forming the film sleeve;

a first molding plate having at least one first molding indentation for the base film section;

a second molding plate having at least one second molding indentation for the cover film section;

said at least one first molding indentation having a one-dimensionally curved cross-sectional shape in a region of the base film section;

said second molding indentation having a one-dimensionally curved cross-sectional shape in a region of the cover film section;

a first placement arrangement for strain-free placement of the base film section into said at least one first molding indentation;

an introduction station for introducing the catheter part into said at least one first molding indentation in addition to the base film section placed into said at least one first molding indentation, wherein the base film section is plastically undeformed; and, a second placement arrangement for strain-free placement of the cover film section into said at least one second molding indentation.

2. The device of claim 1, wherein a plurality of said at least one first molding indentations are formed in said first molding plate and a corresponding number of said at least one second molding indentations are formed in said second molding plate.

3. The device of claim 1, wherein at least one of said first placement arrangement and said second placement arrangement are configured as pressing dies corresponding with a corresponding one of said at least one first molding indentation and said at least one second molding indentation.

4. The device of claim 1, wherein at least one of said first molding plate and said second molding plate are provided with holding arrangements for holding corresponding ones of the base film section placed into said first molding indentation and the cover film section placed into said second molding indentation.

5. The device of claim 4, wherein the holding arrangements are configured as reduced-pressure supplies.

6. The device of claim 1, wherein at least one of said first molding indentation and said second molding indentation is configured as a half-cylinder.

7. The device of claim 1 further comprising a cutting arrangement configured to separate the base film section and the cover film section from a continuous film web.

8. The device of claim 7, wherein said cutting arrangement is arranged in at least one of said first molding station and said second molding station.

9. The device of claim 8 further comprising a sealing heater integrated in at least one of said first molding plate and said second molding plate.

10. The device of claim 8 further comprising a separating station for separating a plurality of sealed catheter parts.

11. A method for sealing a catheter part into a film sleeve via a device including a first molding station, a second molding station, and a sealing station for sealing a base film section and a cover film section onto one another and onto sealing faces of the catheter part while forming the film sleeve, the device further including a first molding plate having a first molding indentation for the base film section and a second molding plate having a second molding indentation for the cover film section, the first molding indentation and the second molding indentation having a one-dimensionally curved cross-sectional shape in a region of the base film section and of the cover film section, respectively, the device further including a first placement arrangement for strain-free placement of the base film section into the at least one first molding indentation, the device further including an introduction station for introducing the catheter part into the at least one first molding indentation in addition to the base film section placed into the first molding indentation wherein the base film is plastically undeformed, the device further including a second placement arrangement for strain-free placement of the cover film section into the at least one second molding indentation, the method comprising:

in the first molding station, placing the base film section without strain into the first molding indentation of the first molding plate;

in the introduction station, introducing the catheter part with the base film section, which is plastically undeformed and placed into the first molding indentation;

in the second molding station, placing the cover film section without strain into the second molding indentation of the second molding plate; and, in the sealing station, sealing the catheter part sealed into the film sleeve by the first molding plate and the second molding plate being brought together with the base film section put in place, with the cover film section put in place and with the catheter part introduced, the base film section and the cover film section being sealed onto one another at common sealing sections and being sealed onto sealing faces of the catheter part while forming the film sleeve.

* * * * *